(12) United States Patent
Sabb et al.

(10) Patent No.: US 6,784,172 B2
(45) Date of Patent: Aug. 31, 2004

(54) PROCESSES FOR PREPARATION OF CYCLOPENTA[B][1,4]DIAZEPINO[6,7,1-HI] INDOLES AND DERIVATIVES

(75) Inventors: Annmarie Louise Sabb, Pennington, NJ (US); Robert Lewis Vogel, Stratford, NJ (US); Madelene Miyoko Antane, West Windsor, NJ (US); Panolil Raveendranath, Monroe, NY (US); Sreenivasulu Megati, New City, NY (US); Michael David Smith, Martinez, CA (US); James Albert Nelson, Washington Crossing, PA (US)

(73) Assignee: Wyeth, Madison, NJ (US)

( * ) Notice: Subject to any disclaimer, the term of this patent is extended or adjusted under 35 U.S.C. 154(b) by 229 days.

(21) Appl. No.: 10/016,420

(22) Filed: Nov. 2, 2001

(65) Prior Publication Data

US 2002/0062022 A1 May 23, 2002

Related U.S. Application Data

(60) Provisional application No. 60/245,954, filed on Nov. 3, 2000.

(51) Int. Cl.[7] .................. A61K 31/55; A61P 25/00; A61P 25/24; C07D 243/00
(52) U.S. Cl. .................. 514/219; 540/555; 540/556
(58) Field of Search .................. 514/219; 540/555, 540/556

(56) References Cited

U.S. PATENT DOCUMENTS

| | | | |
|---|---|---|---|
| 3,914,250 A | 10/1975 | Kim | 260/315 |
| 6,503,900 B2 | 1/2003 | Sabb et al. | 514/219 |
| 2002/0055504 A1 | 5/2002 | Chan | 514/219 |
| 2002/0055630 A1 | 5/2002 | Welmaker et al. | 540/556 |
| 2002/0058689 A1 | 5/2002 | Welmaker et al. | 514/411 |
| 2002/0107242 A1 | 8/2002 | Saab et al. | 514/219 |
| 2002/0119966 A1 | 8/2002 | Saab et al. | 514/219 |
| 2002/0128261 A1 | 9/2002 | Saab et al. | 514/219 |

FOREIGN PATENT DOCUMENTS

| | | |
|---|---|---|
| WO | WO 96/29316 | 9/1996 |
| WO | WO 00/35922 | 6/2000 |
| WO | WO 02/08186 | 1/2002 |

OTHER PUBLICATIONS

Gregory E. Martin et al., J. Med. Chem., 1989, 1052–1056, 32.
J.L. Browning et al., Society for Neuroscience Abstracts, Oct. 1999, 2075, 25(2), Abstract 830.12.
Jackson B. Hester et al., J. Med. Chem., 1970, 827–835, 13.
Dong H. Kim, J. Heterocycl. Chem., 1976, 1187–92, 13(60.
S. Archer et al., J. Am. Chem. Soc., 79, 5783–5785 (1957).
L. Zhang et al., Tetrahedron Letters, 36(46), 8387–8390 (1995).
G.E. Stokker, Tetrahedron Letters, 37(31), 5453–5456 (1996).
Cuadro et al., Synthetic Communications, 21(4), 535–544 (1991).
W. Perkin et al., J. Chem. Soc., 123, 3242–3247 (1923).
H. Booth et al., J. Chem. Soc., 158, 2302–2311 (1958).
Haerter et al., Chimia, 30(2), 50–52 (1976).
D.H. Kim, J. Heterocyclic Chem., 13, 1187–1192 (1976).

*Primary Examiner*—Brenda Coleman
(74) *Attorney, Agent, or Firm*—Kimberly R. Hild

(57) ABSTRACT

This invention provides processes for synthesizing compounds of formula I:

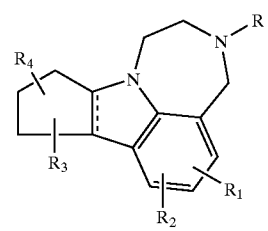

I wherein R is H or alkyl; $R_1$, $R_2$ are H, alkyl, alkoxy, halogen, fluorinated alkyl, —CN, alkyl sulfonamide, alkyl amide, amino, alkylamino, dialkylamino, fluorinated alkoxy, acyl, or aroyl; $R_3$ and $R_4$ are H, alkyl or cycloalkyl; the dashed line indicates an optional double bond; as well as intermediates and pharmaceutically acceptable salts thereof.

10 Claims, No Drawings

PROCESSES FOR PREPARATION OF CYCLOPENTA[B][1,4]DIAZEPINO[6,7,1-HI] INDOLES AND DERIVATIVES

This application claims priority from copending provisional application Ser. No. 60/245,954, filed Nov. 3, 2000, the entire disclosure of which is hereby incorporated by reference.

The present invention relates to processes for the preparation of cyclopenta[b][1,4]diazepino[6,7,1-hi]indoles and intermediates and derivatives thereof, which are serotonin 5-hydroxytryptamine $2_C$ ($5HT_{2C}$) receptor agonists useful for the treatment and prevention of disorders such as obsessive-compulsive disorder, depression, anxiety, schizophrenia, migraine, sleep disorders, eating disorders, obesity, epilepsy, and spinal cord injury.

BACKGROUND OF THE INVENTION

Obesity is a medical disorder characterized by an excess of body fat or adipose tissue. Comorbidities associated with obesity are Type II diabetes, cardiovascular disease, hypertension, hyperlipidemia, stroke, osteoarthritis, sleep apnea, gall bladder disease, gout, some cancers, some infertility, and early mortality. As the percentage of obese individuals continues to rise both in the U.S. and abroad, obesity is expected to be a major health risk in the $21^{st}$ Century. The serotonin 5-hydroxytryptamine (5-HT) receptor is a G-protein coupled receptor which is expressed in neurons in many regions of the human central nervous system. [Wilkinson, L. O. and Dourish, C. T. in *Serotonin Receptor Subtypes: Basic and Clinical Aspects* (ed. Peroutka, S. J. ) 147–210 (Wiley-Liss, New York, 1991).] The $5HT_{2C}$ receptor (formerly called the $5HT_{1C}$ receptor) is a prominent subtype of the serotonin receptor found in the central nervous system of both rats and humans. It is expressed widely in both cortical and subcortical regions. [Julius, D. MacDermott, A. B., Axel, R. Jessell, T. M. *Science* 241:558–564 (1988).] Studies in several animal species and in humans have shown that the non-selective $5HT_{2C}$ receptor agonist, meta-chlorophenylpiperazine (MCPP) decreases food intake. [Cowen, P. J., Clifford, E. M. , Williams, C., Walsh, A. E. S., Fairburn, C. G. *Nature* 376: 557 (1995).] Tecott, et al have demonstrated that transgenic mice lacking the $5HT_{2C}$ receptor eat more and are heavier than Wild Type mice. [Tecott, L. H., Sun, L. M., Akana, S. F., Strack, A. M., Lowenstein, D. H., Dallman, M. F., Jullus, D. *Nature* 374: 542–546 (1995).] Compounds of this invention are $5HT_{2C}$ receptor subtype selective agonists which are selective over other monoamine receptors, cause a reduction in food intake and result in a reduction in weight gain. Other therapeutic indications for $5HT_{2C}$ agonists are obsessive compulsive disorder, depression, panic disorder, schizophrenia, sleep disorders, eating disorders, and epilepsy.

U.S. Pat. No. 3,914,250 (Oct. 21, 1975) describes 1,4-diazepino[6,5,4-jk]carbazoles as anticonvulsant agents. Compounds of this invention are not carbazoles. Compounds of this invention contain a unique ring system not previously described in the literature. This invention relates to cyclopenta[b][1,4]diazepino[6,7,1-hi]indoles and derivatives which bind to and activate $5HT_{2C}$ receptors in the CNS and are useful for the treatment of CNS disorders which can benefit from modulation of the $5HT_{2C}$ receptor.

DESCRIPTION OF THE INVENTION

This invention provides a process for the synthesis compounds of formula I:

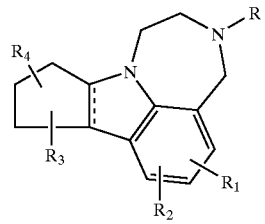

wherein
R is hydrogen or alkyl of 1–6 carbon atoms;
$R_1$, $R_2$ are each, independently, hydrogen, alkyl of 1–6 carbon atoms, alkoxy of 1–6 carbon atoms, halogen, fluorinated alkyl of from 1 to 6 carbon atoms, —CN, —NH—SO$_2$-alkyl of 1–6 carbon atoms, —SO$_2$—NH—alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, or aroyl, preferably phenoyl or thiophenoyl;
$R_3$, $R_4$ are each independently hydrogen, $C_1$–$C_6$ alkyl, cycloalkyl of from 3 to 7 carbon atoms or —CH$_2$-cycloalkyl of from 3 to 7 carbon atoms;
wherein the dashed line indicates an optional double bond;
as well as intermediates and pharmaceutically acceptable salts thereof.

One group of compounds prepared by this invention are those of formula I, above, in which R is hydrogen and $R_1$, $R_2$, $R_3$, and $R_4$ are as defined above. Another process of this invention provides compounds of Formula I wherein R, $R_1$ and $R_3$ are hydrogen and $R_2$ and $R_4$ are as defined above. In another process of this invention, each of R, $R_1$, $R_2$, $R_3$, and $R_4$ are hydrogen. Each of these processes includes a subset wherein the double bond indicated in Formula I by the dashed line is present and another subset wherein a single bond is present.

These compounds are $5HT_{2C}$ receptor agonists useful for the treatment or prevention of disorders involving the central nervous system such as obsessive-compulsive disorder, depression, anxiety, generalized anxiety disorder, panic disorder, schizophrenia, migraine, sleep disorders, eating disorders, obesity, epilepsy, and spinal cord injury.

The compounds of this invention contain asymmetric carbon atoms and thus give rise to optical isomers and diastereoisomers. While shown without respect to stereochemistry in Formula I, the present invention provides for preparation of such optical isomers and diastereoisomers; as well as the racemic and resolved, enantiomerically pure R and S stereoisomers; as well as other mixtures of the R and S stereoisomers and pharmaceutically acceptable salts thereof.

In the definitions of $R_1$ and $R_2$ herein, the fluorinated alkyl and fluorinated alkoxy groups indicate the specified alkyl or alkoxy groups having any amount of fluorine substitution including, but not limited to, groups such as —CHF$_2$, —CF$_3$, —C$_2$F$_5$, —OCF$_3$, etc.

The term "alkyl" includes both straight- and branched-chain saturated aliphatic hydrocarbon groups and cycloalkyl groups. Halogen is defined as Cl, Br, F, and l.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. The processes described herein will be understood to optionally include an additional step of preparing a pharmaceutically acceptable salt of a compound of Formula I, as defined herein, utilizing processes and methods known in the art.

The 5HT$_{2C}$ receptor agonists of this invention are useful for the treatment or prevention in mammals, preferably in humans, of disorders involving the central nervous system such as obsessive-compulsive disorder, depression, atypical depression, bipolar disorders, anxiety, generalized anxiety disorder, schizophrenia, psychoses, personality disorders, organic mental disorders, behavioral disorders associated with dementia or age-related conditions, aggressivity, drug and alcohol addiction, social phobias, sexual dysfunction, panic disorder, migraine, sleep disorders, such as sleep apnea, eating disorders, such as hyperphagia, bulimia or anorexia nervosa, obesity, epilepsy, and premenstrual tension.

This invention also includes methods of utilizing the compounds herein in treatments or preventitive regimens for treatment of central nervous system deficiencies associated with trauma, stroke, neurodegenerative diseases or toxic or infective CNS disorders including, but not limited to, encephalitis or menengitis; or cardiovascular disorders, including thrombosis; gastrointestinal disorders such as malfunction of gastrointestinal motility; and diabetes insipidus. These methods include the improvement or inhibition of further degradation of central nervous system activity during or following the malady or trauma in question. Included in these improvements are maintenance or improvement in motor and motility skills, control, coordination and strength.

Preferred compounds prepared using this invention are those in which R is hydrogen. Especially preferred are compounds which are enantiomerically pure stereoisomers of compounds where R is hydrogen and the pyrrole ring is reduced.

DETAILED DESCRIPTION OF THE INVENTION

This invention provides a process for preparation of compounds of Formula I,

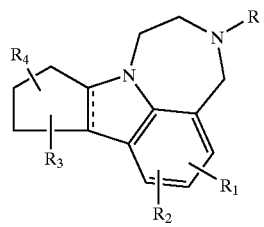

wherein R, $R_1$, $R_2$, $R_3$, and $R_4$ are as defined above. The process comprises the following steps, wherein the dashed line indicates an optional double bond and each of R, $R_1$, $R_2$, $R_3$, and $R_4$ may be as defined in the groups above:

a) treating a benzodiazepine compound of the formula:

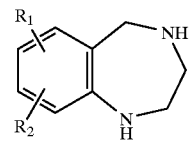

with an acylating agent, such as a base in the presence of a polar solvent, to give an acylated benzodiazepine of the formula:

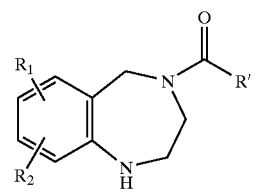

wherein $R^1$ represents alkyl of from 1 to 10 carbon atoms, preferably 1 to 6 carbon atoms, or a benzyl or napthyl group;

b) reacting the acylated benzodiazepine of step a) with a nitrosating agent to provide an acylated nitroso benzodiazepine compound of the formula:

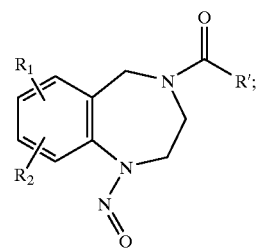

c) reducing the acylated nitroso benzodiazepine compound of step b) to yield an acylated 1-aminobenzodiazepine compound of the formula

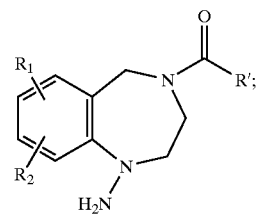

d) allowing the acylated 1-aminobenzodiazepine compound of step c) to react with a cyclopentanone compound of the formula:

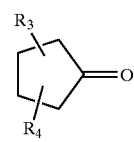

to provide a cyclopentylideneamino benzodiazepine compound of the formula:

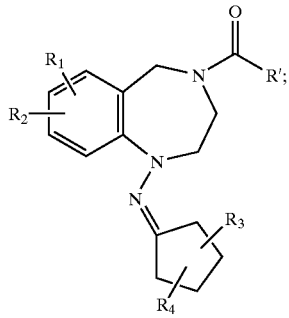

e) reacting the cyclopentylideneamino benzodiazepine compound of step d) to provide an acylated compound of the formula:

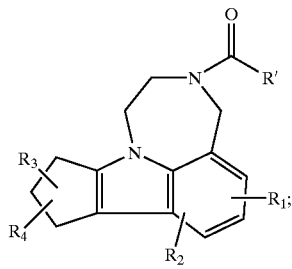

and either
f) deacylating the acylated compound of step e) to provide a compound of the formula:

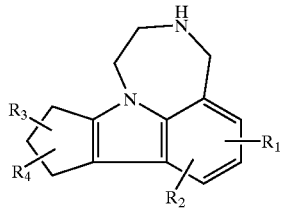

such as with a base in the presence of a polar solvent, which may optionally be reduced; or
g) reducing the acylated compound of step e) to provide a compound of the formula:

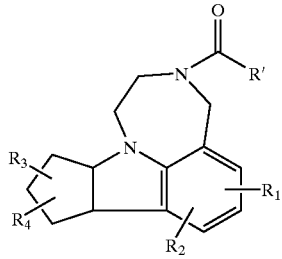

and h) treating the compound of step g) with a deacylating agent to provide a compound of the formula:

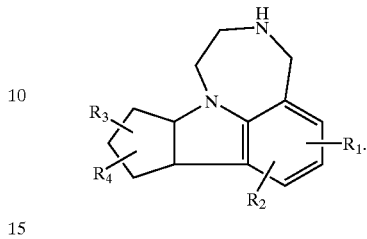

One embodiment of this invention provides a process for the production of compounds of the formula:

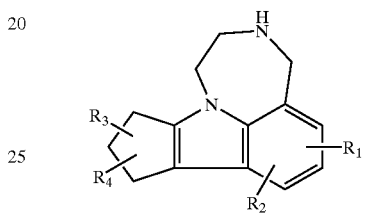

comprising the steps 1 through 6, above, with a further optional step of reducing the compound to produce a compound of the formula:

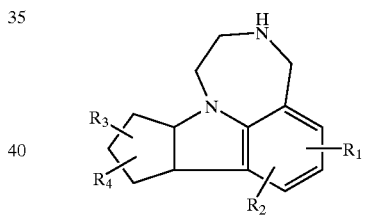

wherein R, $R_1$, $R_2$, $R_3$, and $R_4$ are as defined above.

Another aspect of this invention provides a process comprising steps 1 through 5, above, to provide an acylated compound of the formula:

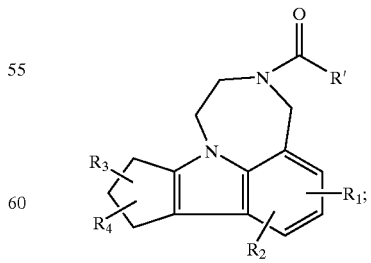

followed by reduction of this compound to provide a reduced acylated compound of the formula:

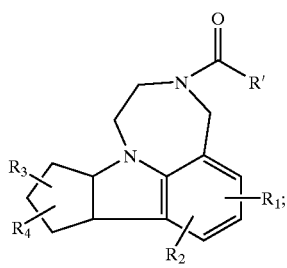

and a deacylation step to provide a compound of the formula:

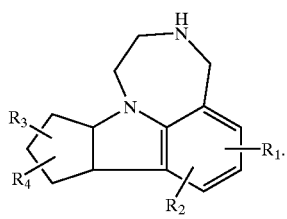

Each of processes described herein further optionally comprise the initial step wherein the benzodiazepine compound of step 1, above, is initially prepared by reduction of a corresponding substituted or unsubstituted benzodiazepinedione, as shown below.

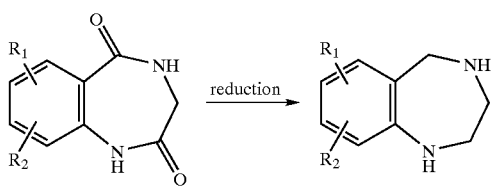

Each of the processes herein also further comprises the optional step of alkylating the compounds of the formula:

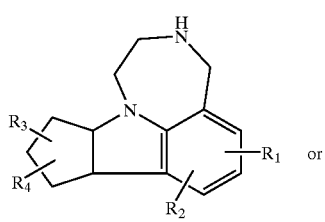

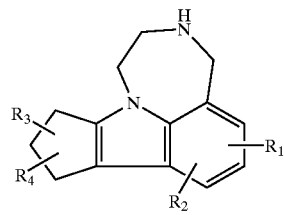

wherein $R_1$, $R_2$, $R_3$, and $R_4$ are as defined herein, to provide an alkylated compound of the formula:

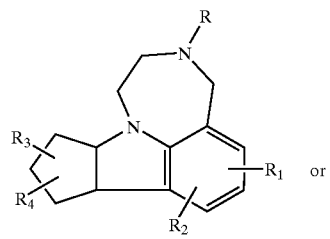

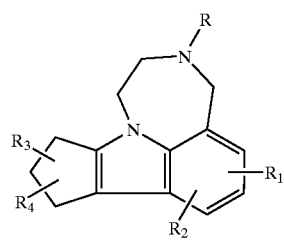

wherein R represents an alkyl group of from 1 to 6 carbon atoms.

The following non-limiting scheme further illustrates the synthesis of compounds according to this invention, which may be accomplished from commercially available starting materials or starting materials which can be prepared using literature procedures.

Scheme 1

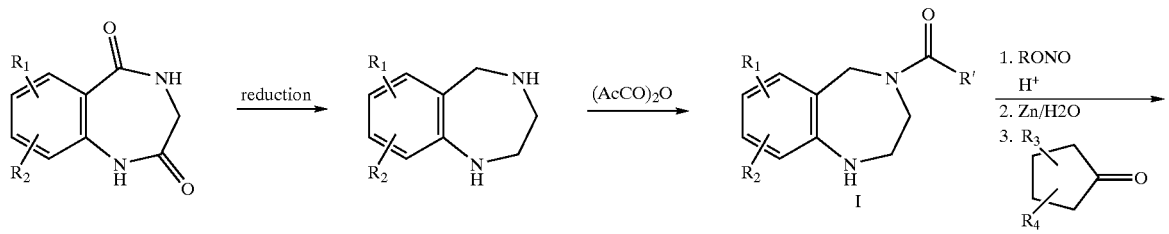

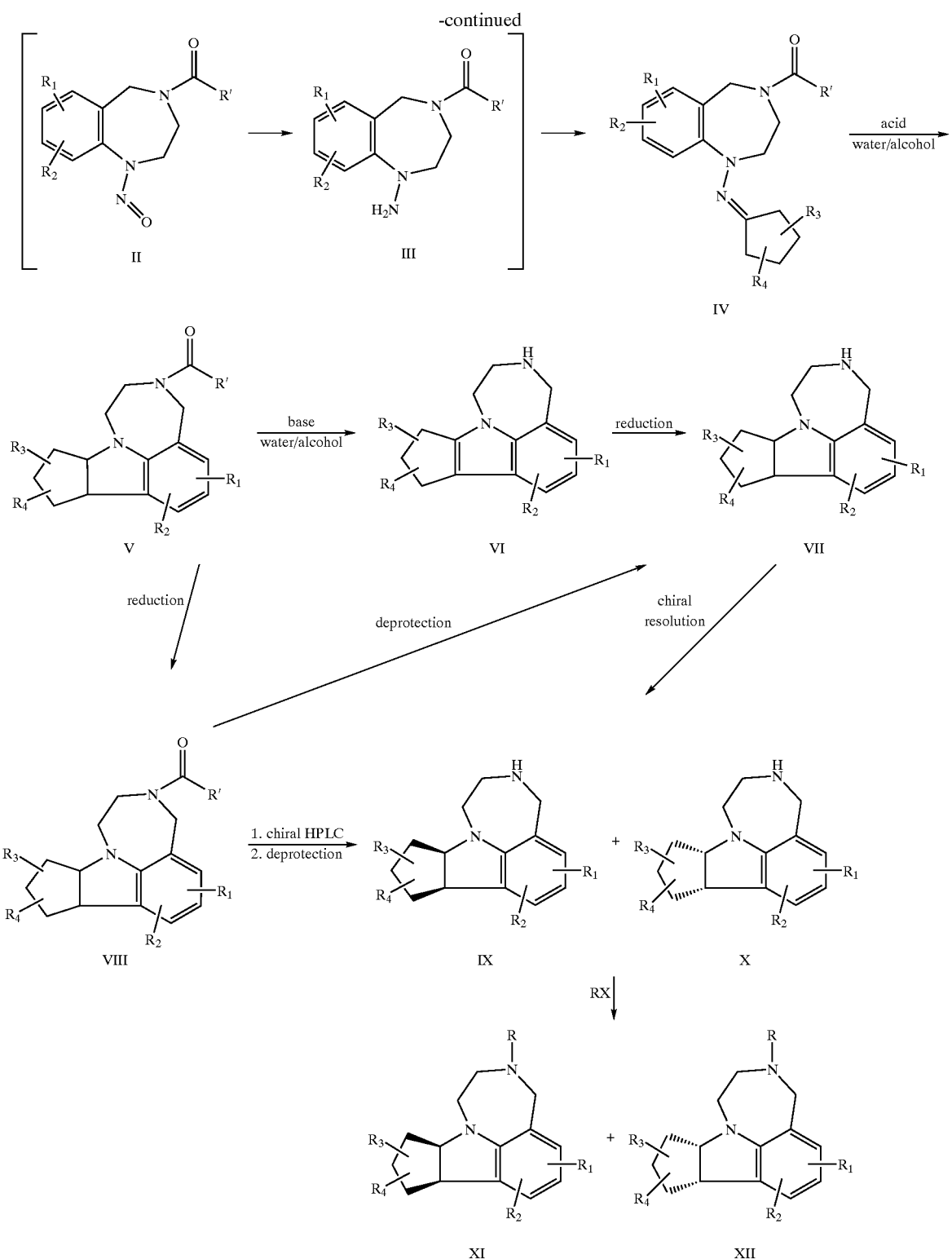

In Scheme 1, a substituted or unsubstituted benzodiazepinedione is reduced with a reducing agent, such as lithium aluminum hydride or a borane-tetrahydrofuran complex, to give a substituted or unsubstituted benzodiazepine. The basic nitrogen of the benzodiazepine is protected, such as by being treated with an acylating reagent, such as acetic anhydride, in the presence of a base, such as triethylamine or potassium carbonate, in an organic solvent, such as ether or acetonitrile, to give intermediate I. Intermediate I is allowed to react with an organic or inorganic nitrosating agent, such as t-butyl nitrite or sodium nitrite, in the presence of an acid, such as acetic acid or hydrochloric acid, to give nitroso compounds II. The nitroso compounds II are reduced to hydrazines III using a reducing agent, such as zinc powder in acetic acid and water. The hydrazines III are allowed to react with substituted or unsubstituted cyclopentanones in an acid, such as acetic acid, at 25–110° C., to give substituted or unsubstituted hydrazones IV. The hydrazones IV are treated with an acid, such as sulfuric acid or p-toluenesulfonic acid, in the presence of water or an alcohol, such as 1-propanol, at elevated temperatures such as 50–110° C. to give protected fused indoles V. The protected fused indoles V can be treated with a base, such as NaOH, in a polar solvent, such as water or an alcohol, at elevated temperatures, such as 50–110° C. to give the deprotected fused indoles VI, which are products of this invention. Indoles VI can be reduced using catalytic hydrogenation over a catalyst, such as palladium on charcoal, in the presence of a acid, such as trifluoroacetic acid or hydrochloric acid, to give indolines VII, which are products of this invention. In addition, protected fused indoles V can be reduced, such as by catalytic hydrogenation over a catalyst, such as palladium on charcoal, in an organic solvent, such as ethanol, in the presence of an acid, such as trifluoroacetic acid or hydrochloric acid, to give protected fused indolines VIII. Protected fused indolines VIII are racemic or diastereomeric mixtures which can be separated using chiral HPLC to give separated enantiomers or diastereoisomers which can then be treated with an inorganic base, such as NaOH in a polar solvent, such as water or methanol at elevated temperatures, such as 50–100° C., to remove the acyl group giving enantiomers or diastereoisomers IX and X which are products of this invention. Fused indolines VIII can also be deprotected using an inorganic base, such as KOH, in a polar solvent, such as a mixture of water and methanol, to give fused indolines VII. Enantiomers of fused indolines VII can also be resolved using a resolving agent, such as benzoyltartaric acid, in an organic solvent, such as an alcohol, to give products of this invention. Treatment of the secondary amine of IX and X with an alkylating agent, such as an alkyl halide, gives XI and XII which are compounds of this invention.

An alternate syntheic route to hydrazines III is described in Scheme 2. Substituted or unsubstituted benzodiazepines I are allowed to react with allyl N-[(mesitylsulfonyl)oxy] carbamate in toluene under reflux to give compounds XII. Compounds XII are allowed to react with a catalytic amount of tetrakis triphenylphosphinepalladium and a base, such as diethylamine, in an organic solvent, such as methylene chloride, to give hydrazines III. Hydrazines III are converted to fused indoles V as described in Scheme 1.

Scheme 2

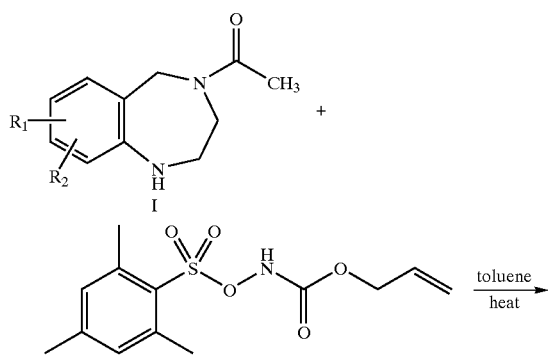

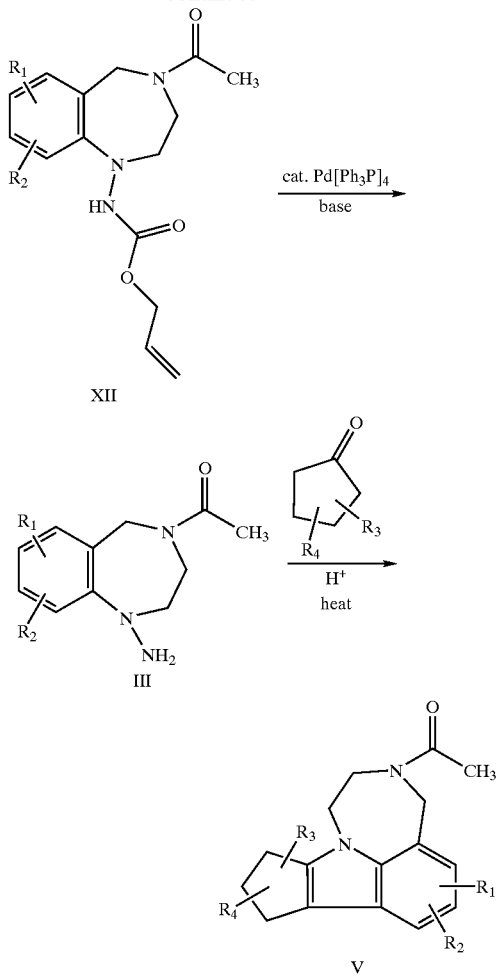

An alternate route to hydrazones IV is described in Scheme 3. Substituted or unsubstituted benzodiazepines I are allowed to react with an inorganic cyanate, such as sodium cyanate, in an organic solvent, such as acetonitrile, in the presence of an acid, such as trifluoroacetic acid, at elevated temperatures, such as 35–75° C. to give ureas XIII. Ureas XIII are treated with an inorganic hypochlorite, such as sodium hypochlorite, in an alcohol-water solution at 0–25° C. to give hydrazines III. Hydrazines III in solution are cooled to <25° C. and treated with acetic acid and substituted or unsubstituted cyclopentanones and warmed to room temperature to give hydrazones IV. Hydrazones IV are converted to fused indoles V as described in Scheme 1.

It will be understood that the processes of this invention can further include analogous steps wherein the protecting group applied to the optionally substituted benzodiazepines of Formula I in Scheme 1 are other than the acetyl group used above. Other conventional protecting groups known in the art may also be used including, but not limited to alkyl and acyl chlorides, alkyl or aryl chloroformates, such as ethylchloroformate and benzyl chloroformate and dialkylcarbonates, and para-nitro benzene sulfonyl chloride.

The acylation steps of this invention are understood to include reactions of the appropriate compound with any acylating agent and reaction conditions known in the art. Useful in these steps are acylating agents include acid halides and esters or anyhrides of the appropriate aliphatic carboxylic acid. Useful acid halides include acetyl chloride, propionyl chloride, isobutyryl chloride, benzoyl chloride, etc. Acid anhydrides include acetic anhydride and benzoic anhydride. Similarly, alkylation steps herein are understood to include any relevant alkylating agents and conditions known in the art. These include, but are not limited to the use of alkyl halides, such as methyl iodide, or alkyl tosylates or aldehyde alkylating agents in the presence of an applicable reducing agent.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids. The processes herein will be understood to include an optional additional step of forming a salt form of the products via standard addition reactions with any pharmaceutically acceptable organic or inorganic acid.

A method of resolving the (R,R) enantiomer from racemic mixtures of these compounds comprises the steps of:
  a) dissolving about 1 equivalent of the racemic compound mixture of a product of this invention in a solubilizing amount of an alcohol resolving agent at a temperature of from about 50° C. to the reflux temperature for the alcohol, preferably between about 50° C. and 70° C., under an inert atmosphere, to create a resolving solution;
  b) treating the resolving solution of step a) with from about 0.1 to about 0.35 equivalents of dibenzoyl-L-tartaric acid, preferably from about 0.15 equivalents to about 0.3 equivalents, more preferably from about 0.23 to about 0.27 equivalents, most preferably about 0.25 equivalents to precipitate the desired (R,R) enantiomer from the resolving solution as the corresponding tartaric acid salt form; and
  c) separating the desired enantiomer from the resolving solution through conventional means, such as filtration.

It will be understood that this process may be followed by additional steps of filtration and purification to enhance the purity and yield of the desired enantiomer product in question.

In step b) it is preferred that the temperature of the resolving solution be maintained at a temperature at or above about 50° C., preferably nearer to the reflux temperature of the alcohol in question. The alcohol component of step a) may be comprise a single alcohol or a combination of two or more alcohols selected from those known in the art into which the compound in question can be dissolved. Among the preferred alcohols are the commercially available and relatively low boiling alcohols comprising 10 carbon atoms or less including methanol, ethanol, n-propanol, isopropanol, n-butanol, t-butanol, cyclohexanol, etc.

It will also be understood that the (S,S) enantiomer of the racemic mixture mentioned above could then be purified and collected from the remaining resolving solution described above after collection of the (R,R) tartaric acid salt.

An analogous method for resolving the (S,S) enantiomer from the racemic mixtures of compounds of this invention, the method comprising the steps a) through c) listed above, with dibenzoyl-D-tartaric acid being used in place of dibenzoyl-L-tartaric acid in step b). Comparably, the (R,R) enantiomer can be collected and purified by conventional means from the remaining solution after the tartaric acid salt form of the (S,S) enantiomer is precipitated and removed in this analogous method.

The following examples illustrate compound preparations representative of this invention.

EXAMPLE 1

1,2,3,4,9,10-Hexahydro-8H-cyclopenta[b][4,1]diazepino[6,7,1-hi]indole

To a suspension of benzodiazapine (92.0 g, 0.62 mole) and $K_2CO_3$ (90.2 g, 0.65 mole, −325 mesh) in $CH_3CN$ (1000 ml) was added acetic anhydride (63.4 g, 58.6 ml, 0.62 mole) in 0.5 h (reaction mixture was cooled in ice water to maintain the reaction mixture temperature between 15–22° C.). The suspension was stirred for 0.5 h at room temperature (check TLC after 30 min, eluent ethyl acetate:MeOH 9:1). The reaction mixture was evaporated and to the residue water (400 ml) was added. The suspension was cooled in ice, filtered, washed with cold water (50 ml×2). Dried under vacuum to give 109.7 g of 4-acetylbenzodiazepine as a white solid, yield 93%).

Preparation of Hydrazine (4-acetyl-2,3,4,5-tetrahydro-1H-1,4-benzodiazepin-1-ylamine 4-Acetylbenzodiazepine (28.5 g, 50.15 m) and allyl N-[(mesitylsulfonyl)-oxy]carbamate (53.8 g, 0.18 m) were combined in toluene (270 mL) and heated under reflux for 2.5 h. The reaction was quenched with 0.5 N NaOH. The precipitate that formed was removed by filtration and the aqueous filtrate was extracted with ethyl acetate (3×). The combined organic layers were washed with saturated sodium chloride solution, dried ($MgSO_4$), and evaporated to give a residue which was dissolved in methylene chloride (490 mL) and treated with diethylamine (51 mL, 5 eq.) and tetrakis triphenylphosphinepalladium (115 mg, 0.001 eq). After stirring for 2 h at room temperature, the volatiles were removed under reduced pressure and the residue was purified by chromatography on silica gel eluting with 10–20% methanol in ethyl acetate to give 4-acetyl-2,3,4,5-tetrahydro-1H-1,4-benzodiazepin-1-ylamine (13.5 g, 44%) as a white solid.

Preparation of Hydrazone

4-Acetyl-N-cyclopentylidene-2,3,4,5-tetrahydro-1H-1,4-benzodiazepin-1-amine

4-Acetyl-2,3,4,5-tetrahydro-1H-1,4-benzodiazepine (30 g, 0.158 m) was dissolved in glacial acetic acid (287 mL). Tert-butylnitrite (20.6 mL) was added and the reaction mixture was stirred at room temperature. Meanwhile, a 2L round-bottomed flask was equipped with an mechanical overhead stirrer, nitrogen inlet tube, and a dropping funnel. Powdered zinc (32.8 g) was suspended in water (88 mL) with vigorous stirring. When a TLC (silica gel, 5% methanol in methylene chloride) indicated that all of the benzodiazepine had been converted to the nitroso compound, the zinc-water mixture was cooled in an ice bath and the nitroso solution was added dropwise over 1.5 h with vigorous stirring. When all of the nitroso solution had been added, the ice bath was removed and stirring was continue for another 30 minutes. Cyclopentanone (41.8 mL) was added to the reaction vessel containing the hydrazine (generated in situ) which was then placed in a preheated oil bath and heated at 75–85° C. (internal temperature.) Heating was continued until there was no more hydrazine as indicated by TLC on silica gel eluting with 10% methanol in ethyl acetate (2 h). After cooling to room temperature, the reaction mixture was diluted with methylene chloride (600 mL) and stirred at room temperature. The insoluble material was separated by filtration and washed with methylene chloride (3×100 mL). The layers were combined and evaporated to give crude hydrazone, 64 g.

3-Acetyl-1,2,3,4,10-hexahydro-8H-cyclopenta[b][4,]diazepino[6,7,1-hi]indole

The crude hydrazone (64 g) was dissolved in 1-propanol (385 mL). p-Toluene-sulfonic acid hydrate (32 g) was added and the reaction vessel was placed in a pre-heated oil bath. The reaction mixture was heated under reflux for about 2.5 h (TLC analysis showed no hydrazone remaining). The heating bath was removed and the reaction mixture was stirred for an additional 15 minutes at room temperature. The reaction mixture was diluted with ethyl acetate (1200 mL) and cooled in an ice bath. 2.5 N NaOH was added with cooling and stirring until the aqueous phase remained basic (indicator paper, pH 12). The phases were separated and the organic phase was extracted with saturated sodium bicarbonate (2×300 mL). The aqueous phase was back extracted with one portion of ethyl acetate. The organic phases were combined, dried (MgSO$_4$), filtered and evaporated to give a dark brown residue. The residue was purified by column chromatography on silica gel eluting with 0.5–2% methanol in methylene chloride to give, 22.46 g (56%) of 3-acetyl-1,2,3,4,10-hexahydro-8H-cyclopenta[b][1,4]diazepino[6,7,1-hi]indole, as a viscous oil.

3-Acetyl-1,2,3,4,10-hexahydro-8H-cyclopenta[b][1,4]diazepino[6,7,1-hi]indole (2.34 g, 9.20 mmol) was dissolved in MeOH. The solution was diluted with 2.5N NaOH and solid NaOH pellets were added. The reaction mixture was placed in an oil bath at 95° C. for 6 h. then cooled to room temperature and stirred overnight. The volatiles were evaporated under reduced pressure and the residue was partitioned between water and ethyl acetate. The ethyl acetate was separated and evaporated and the residue was dissolved in methylene chloride and purified by chromatography on silica gel eluting with 2–5% methanol in methylene chloride to give the product of Example 1 as a light gray solid 1.56 g (80%), mp: 66–68° C.

Anal. Calcd. for $C_{14}H_{16}N_2$ Theory: % C, 79.21; % H, 7.60; % N, 13.20. Found: % C, 78.81; % H, 7.5; % N, 13.10

EXAMPLE 2

1,2,3,4,8,9,10,10a-Octahydro-7bH-cyclopenta[b][1,4]diazepino[6,7,1-hi]indole

Method A.

The compound of Example 1 (1.56 g, 7.35 mmol) was dissolved in trifluoroacetic acid (53 mL) and cooled in an ice/water bath. 1.5 M BH$_3$ in THF (34 mL) was added dropwise slowly and stirred for an additional 15 min. After the addition was complete, water was added slowly to quench the reaction. This was followed by 2.5 N NaOH and 50% NaOH until the reaction mixture was basic (yellow color disappeared).

After extraction with ethyl acetate (3×), the organic phases were combined and concentrated under reduced pressure to give a residue which was purified by chromatography on silica gel eluting with 3–10% MeOH in methylene chloride to give 600 mg (38%) of the product as a yellow solid: mp 64–68° C.

Anal. Calcd for $C_{14}H_{18}N_2 \cdot 0.2\ H_2O$ Calcd: % C, 77.17; % H, 8.51; % N, 12.86. Found: % C, 77.13; % H, 8.18; % N, 12.61.

Method B.

4-Acetyl-2,3,4,5-tetrahydro-1H-1,4-benzodiazepine-1-carboxamide

To a solution of 4-acetylbenzodiazepine (20.0 g, 0.105 mole) in acetonitrile (100 ml) at room temperature was added sodium cyanate (27.4 g, 0.42 mole). The resulting suspension was heated to 50° C. and then trifluoroacetic acid (24.0 g, 0.21 mole) was added slowly dropwise over 30 min. Heating was continued at 50° C. for 1 h. The reaction mixture was cooled to room temperature and the solvent was evaporated to give a white residue. Water (160 ml) was added to the residue and the mixture was cooled in ice for 1 h. The solids were collected by filtration and washed with cold water. After drying under house vacuum 23.6 g (96%) of product was obtained as a white solid.

NMR (300 MHz, DMSO): δ7.2–7.5 (4H, m), 5.76 (2H, br.s), 4.46 (2H, br.s), 3.61 (2H, br.s), 2.0 (3H, two singlets). GC-MS: 98%. HPLC purity (area %): 97.4% LC-MS: 96.7%.

4-Acetyl-N-cyclopentylidene-2,3,4,5-tetrahydro-1H-1,4-benzodiazepin-1-amine

To a mixture of ethanol (95 ml) and water (95 ml) was added sodium hydroxide pellets (11.5 g, 0.288 mole). The mixture was cooled in an ice bath and then 4-acetyl-2,3,4,5-tetrahydro-1H-1,4-benzodiazepine-1-carboxamide (19.2 g, 0.082 mole) was added. To the milky suspension at 4° C. was added sodium hypochlorite (94.0 ml, 0.164 mole, 10–13%) over 10 min. The reaction mixture was warmed to ambient temperature. A clear solution was observed. After 2 h, the reaction mixture was cooled in an ice bath and acetic acid (82.0 ml) was added. To this solution cyclopentanone (8.3 g, 0.988 mole) was added. After 1.5 h at room temperature the reaction mixture was cooled in an ice bath and neutralized with 10 N sodium hydroxide. The aqueous phase was extracted with ethyl acetate (125 ml, 50 ml×2) and the combined organic layers were washed with brine (200 ml), dried (Na$_2$SO$_4$) and evaporated to give a syrup, 17.8 g (yield 80%) of the hydrazone product. The crude hydrazone was used without purification in the Fischer-Indole cyclization.

LC-MS: 93%. GC-MS: 94%.

3-Acetyl-1,2,3,4,10-hexahydro-8H-cyclopenta[b][1,4]diazepino[6,7,1-hi]indole

To a gummy amber colored hydrazone (0.78 g of 94% pure by GC) was added a solution of 4% aq.H$_2$SO$_4$ (5 ml H$_2$O+0.2 ml Conc.H$_2$SO$_4$). The clear reaction mixture solution was heated to reflux for 1 h. After cooling the reaction mixture, it was extracted with ethyl acetate. The ethyl acetate layer was washed with 5% NaHCO$_3$ solution and saturated sodium chloride solution and dried (MgSO$_4$). Filtration and evaporation of the volatiles from the filtrate gave 0.48 g of 3-acetyl-1,2,3,4,10-hexahydro-8H-cyclopenta[b][1,4]diazepino[6,7,1-hi]indole as an off-white solid (66%).

NMR (300 MHz, DMSO): δ 7.22 (1H, m), 6.8 (2H, m), 4.85 (2H, two singlets), 4.18 (2H, m), 3.98 (2H, m) 2.7 (4H, m), 2.46 (2H, m), 2.04 (3H, two singlets). GC-MS: 98%.

To 5% Pd/C (3.5 g) was added ethanol (360 ml), 3-acetyl-1,2,3,4,10-hexahydro-8H-cyclopenta[b][1,4]diazepino[6,7,1-hi]indole (35.8 g, 0.141 mole) and conc.HCl (13.9 ml, 0.141 mole). The suspension was hydrogenated in a Parr apparatus at 35 psi. for 4 h. The reaction mixture was filtered through Celite, washed with ethanol (100 ml×2) and evaporated to give 46.4 g of crude 3-acetyl-1,2,3,4,8,9,10,10a-octahydro-7bH-cyclopenta[b][1,4]diazepino[6,7,1-hi]indole hydrochloride salt, which was used as such in the next step.

To a flask fitted with a reflux condenser, was added KOH (79.4 g), MeOH (136 ml) and water (36 ml). When KOH was dissolving the reaction mixture exothermed to reflux, then it became a clear solution (Claisen alkali). The above solution (warm or hot) was added to the fused indoline (46.4 g) and the resulting suspension was refluxed for 15 h. On cooling the reaction mixture to room temperature 1,2,3,4,8,9,10,10a-octahydro-7bH-cyclopenta[b][1,4]diazepino[6,7,1-hi]indole crystallized out of the reaction mixture. The solids were collected by filtration and washed with water (50 ml×4). The wet product (28.8 g) was slurried in water (300 ml) at room temperature for 30 min, filtered, washed with water (30 ml×6) and dried under house vacuum at 40° C. for 6 h to give 26.72 g (88.6% over two steps: reduction and deprotection) of the product of Example 2.

HPLC: (97.89% area) NMR (300 MHz, DMSO): δ 6.86 (1H, d, J=7.2 Hz), 6.74 (1H, d, J=7.3 Hz), 6.53 (2H, t, J=7.3 Hz), 3.9 (1H, br.t), 3.81 (1H, d, J=15 Hz), 3.48 (1H, d, J=15 Hz), 3.04–3.15 (2H, m), 2.2 (1H, br.s), 1.85–2.0 (1H, m), 1.73–1.84 (1H, m), 1.34–1.72 (4H, m). GC-MS: 99.9%.

EXAMPLE 3

3-Acetyl-1,2,3,4,8,9,10,10a-octahydro-7bH-cyclopenta[b][1,4]diazepino[6,7,1-hi]indole 3-Acetyl-1,2,3,4,10-hexahydro-8H-cyclopenta[b][1,4]diazepino[6,7,1-hi]indole (2.07 g, 8.12 mmol) was dissolved in EtOH and hydrogenated over 10% Pd on carbon (0.25 g) in a Parr shaker at 55 lbs of hydrogen pressure. After 5 hrs, the reaction mixture was filtered through Celite to remove the catalyst and the filtrate was concentrated under reduced pressure to give a residue which was purified by chromatography on silica gel eluting with 0.3–2% MeOH in methylene chloride to give 1.84 g (87%) of 3-acetyl-1,2,3,4,8,9,10,10a-octahydro-7bH-cyclopenta[b][1,4]diazepino[6,7,1-hi]indole as a white solid, mp:111–113° C.

Anal. Calcd for $C_{16}H_{20}N_2O+0.20\ H_2O$ Theory: % C, 73.93; % H, 7.91; % N, 10.78 Found: % C, 74.05; % H, 7.91; % N, 10.79.

3-Acetyl-1,2,3,4,8,9,10,10a-octahydro-7bH-cyclopenta[b][1,4]diazepino[6,7,1-hi]indole was dissolved in conc. HCl and heated with stirring in an oil bath (110° C.) for 12 hr. After cooling, the reaction mixture was made basic with 2.5N NaOH and 50% NaOH, extracted into methylene chloride, dried (MgSO$_4$), filtered and concentrated to give a residue. The residue was purified by chromatography on silica gel eluting with 1–20% MeOH in methylene chloride to give the product of Example 2 as a yellow solid, mp: 76–79° C.

EXAMPLE 4

The compound of Example 2 was chromatographed on a Chiralal column eluting with MeOH containing 0.1% diethylamine.

Peak one was obtained as a yellow solid, mp: 51–54° C. and identified (7bS,10aS)-1,2,3,4,8,9,10,10a-octahydro-7bH-cyclopenta[b][1,4]diazepino[6,7,1-hi]indole.

Anal. Calcd for $C_{14}H_{18}N_2+0.20\ H_2O$ Theory: % C, 78.46; % H, 8.47; % N, 13.07 . Found: % C, 77.09; % H, 8.50; % N, 12.72.

Peak two was obtained as a yellow solid, mp: 43–46° C. This peak was identified as a mixture of 92.3% (7bR, 10aR)-1,2,3,4,8,9,10,10a-octahydro-7bH-cyclopenta-[b][1,4]diazepino[6,7,1-hi]indole and 7.7% of identified (7bS, 10aS)-1,2,3,4,8,9,10,10a-octahydro-7bH-cyclopenta[b][1,4]diazepino[6,7,1-hi]indole

EXAMPLE 5

3-Acetyl-1,2,3,4,8,9,10,10a-octahydro-7bH-cyclopenta[b][1,4]diazepino[6,7,1-hi]indole (Example No. 3) was chromatographed on a Chiralcel AD chiral column (20×250 mm) eluting with 100% MeOH at room temperature, detection method: UV/VIS at 254 nm.

A. Peak one was obtained as a colorless viscous oil, identified as (7bS,10aS)-3-acetyl-1,2,3,4,8,9,10,10a-Octahydro-7bH-cyclopenta[b][1,4]diazepino[6,7,1-hi]indole (WAY-164993).

Anal. Calcd. for $C_{16}H_{20}N_2O+.0.60\ H_2O$ Theory: % C, 71.93; % H, 8.00; % N, 10.49. Found: % C, 72.06; % H, 7.79; % N, 10.73. O.R.:[alpha]25/D=+118(19.2 mg/mL) MeOH)

(7bS, 10aS)-3-Acetyl-1,2,3,4,8,9,10,10a-octahydro-7bH-cyclopenta[b][1,4]-diazepino[6,7,1-hi]indole was treated with solid NaOH in MeOH under reflux to give (7bS, 10aS)-1,2,3,4,8,9,10,10a-octahydro-7bH-cyclopenta-[b][1,4]diazepino-[6,7,1-hi]indole (WAY-163907) mp: 54–56° C.

O.R.: [alpha]25/D=+134.18 (10.359 mg/mL, MeOH)

B. Peak two was obtained as a colorless viscous oil, identified as (7bR,10 aR)-3-acetyl-1,2,3,4,8,9,10,10a-octahydro-7bH-cyclopenta[b][1,4]diazepino[6,7,1-hi]indole (WAY-164994)

Anal. Calcd. for $C_{16}H_{20}N_2O+.0.80\ H_2O$ Theory: % C, 70.98; % H, 8.04; % N, 10.35. Found: % C, 70.94; % H, 7.73; % N, 10.22. O.R.: [alpha]25/D=−132 (10.2 mg/mL MeOH)

(7bR, 10aR)-3-Acetyl-1,2,3,4,8,9,10,10a-octahydro-7bH-cyclopenta-[b][1,4]diazepino[6,7,1-hi]indole was treated with solid NaOH in MeOH under reflux to give 7bR, 10 aR)-1,2,3,4,8,9,10,10a-octahydro-7bH-cyclopenta-[b][1,4]diazepino[6,7,1-hi]indole (WAY-163909) mp: 57–59° C.

Anal Calcd for $C_{14}H_{18}N_2$ Theory: % C, 77.81; % H, 8.49; % N, 12.96. Found: % C, 78.01; % H, 8.64; % N, 12.90.

EXAMPLE 6

Chiral Salt Resolution of Example No. 2

(7bR,10aR)-1,2,3,4,8,9,10,10a-octahydro-7bH-cyclopenta-[b][1,4]diazepino[6,7,1-hi]indole The compound of Example 2 (10.0 g, 46.7 mmol) was dissolved in isopropanol (500 mL) at 65–70° C. under nitrogen and dibenzyol-L-tartaric acid (4.18 g, 11.7 mmol) was added all at one time. The resultant solids were slurried at 70–75° C. for two h, cooled to room temperature and stored at 10° C. for 12 h. The solids were filtered and washed twice with isopropanol (15 mL). The solids were reslurried in hot (80° C.) isopropanol (400 mL) for 1.5 h, cooled to room temperature and stored at 10° C. for 12 h. The solids were filtered and washed twice with isopropanol (15 mL) and air dried to give 7.3 g (79.9%) of the dibenzoyl-L-tartaric acid salt of the title compound as a white solid, mp: 163–5° C.

Anal. Calcd for $C_{14}H_{18}N_2.0.5\ C_{18}H_{14}O_8.0.4\ C_3H_8O$ Calcd: % C, 69.60; % H, 6.75; % N, 6.70. Found: % C, 69.80; % H, 6.73; % N, 6.58. O.R.: [alpha]25/D=−138.4 (1 mg/mL, MeOH)

The above tartrate salt (9.5 g, 12.1 mmol) was slurried in ethyl acetate (950 mL) and 1 N hydrochloric acid was added (25.0 mL, 25.0 mmol). The slurry was concentrated by atmospheric distillation (72–77° C.) to a volume of 275 mL, cooled to room temperature and stored overnight at 10° C. The solids were filtered and washed twice with ethyl acetate (20 mL) and air dried to give 5.7 g (92.8%) of the hydrochloride salt of the title compound as a white solid, mp 246–249° C. decomposed.

The HCl salt (5.6 g) was dissolved in ethanol (100 mL) at reflux. Upon cooling to room temperature, needle-like crystals formed. The mixture was stored overnight at 10° C. The solids were filtered, washed twice with ethanol (10 mL) and vacuum dried (57° C./0.1 mm) to give 3.8 g (67.8%) of white solid, mp 252–253° C. decomposed.

Anal. Calcd for $C_{14}H_{18}N_2 \cdot HCl$ Calcd: % C, 67.05; % H, 7.64; % N, 11.17. Found: % C, 66.74; % H, 7.54; % N, 11.09.

What is claimed:

1. A process for the synthesis of compounds of formula I:

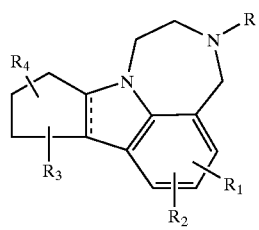

wherein

R is hydrogen;

$R_1$ and $R_2$ are each, independently, selected from the group consisting of hydrogen, alkyl of 1–6 carbon atoms, alkoxy of 1–6 carbon atoms, halogen, fluorinated alkyl of from 1 to 6 carbon atoms, —CN, —NH—$SO_2$-alkyl of 1–6 carbon atoms, —$SO_2$—NH—alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, and aroyl;

$R_3$ and $R_4$ are each independently selected from the group consisting of hydrogen, $C_1$–$C_6$ alkyl, cycloalkyl of from 3 to 7 carbon atoms and —$CH_2$-cycloalkyl of from 3 to 7 carbon atoms;

wherein the dashed line indicates an optional double bond;

the process comprising the steps of:
a) acylating a benzodiazepine compound of the formula:

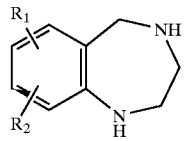

to give an acylated benzodiazepine of the formula:

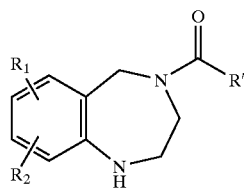

wherein $R^1$ represents alkyl of from 1 to 10 carbon atoms, or a benzyl or napthyl group;

b) reacting the acylated benzodiazepine of step a) with a nitrosating agent to provide an acylated nitroso benzodiazepine compound of the formula:

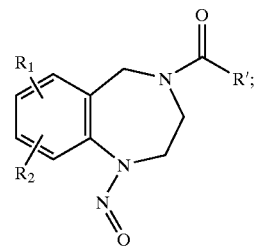

c) reducing the acylated nitroso benzodiazepine compound of step b) to yield an acylated 1-aminobenzodiazepine compound of the formula

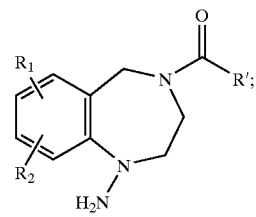

d) allowing the acylated 1-aminobenzodiazepine compound of step c) to react with a cyclopentanone compound of the formula:

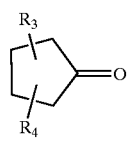

to provide a cyclopentylideneamino benzodiazepine compound of the formula:

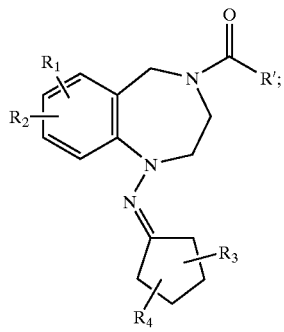

e) reacting the cyclopentylideneamino benzodiazepine compound of step d) to provide an acylated compound of the formula:

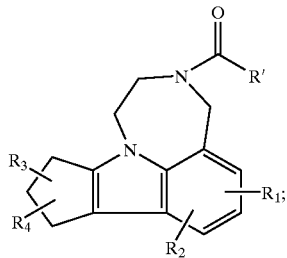

and either f) deacylating the acylated compound of step e) to provide a compound of the formula:

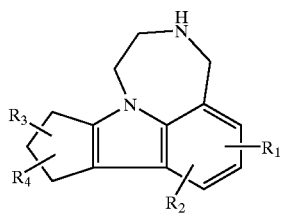

which may optionally be reduced; or g) reducing the acylated compound of step e) to provide a reduced acylated compound of the formula:

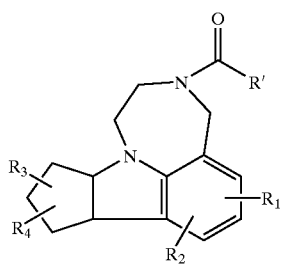

and deacylating the reduced acylated compound of this step g) to provide a compound of the formula:

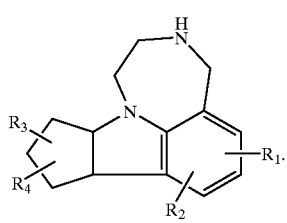

2. A process of claim 1 for the synthesis of compounds of the formula:

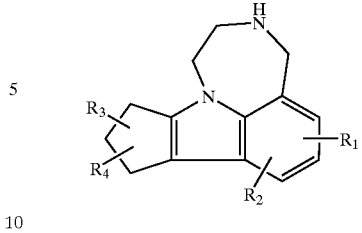

comprising the steps a) through f) of claim 1, wherein $R_1$, $R_2$, $R_3$, and $R_4$ are as defined in claim 1.

3. The process of claim 2 further comprising the step of reducing the compound of the formula:

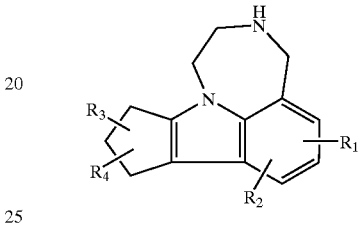

to produce a compound of the formula:

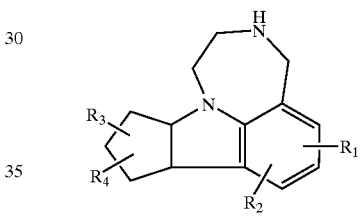

wherein $R_1$, $R_2$, $R_3$, and $R_4$ are as defined in claim 1.

4. The process of claim 3 further comprising the step of alkylating the compound of the formula:

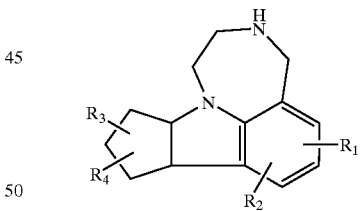

wherein $R_1$, $R_2$, $R_3$, and $R_4$ are as defined in claim 1, to provide an alkylated compound of the formula:

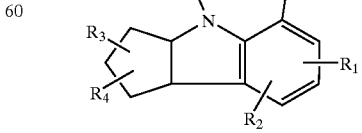

wherein R is an alkyl group of from 1 to 6 carbon atoms.

5. The process of claim 1 comprising the steps a) through e) of claim 1 to provide an acylated compound of the formula:

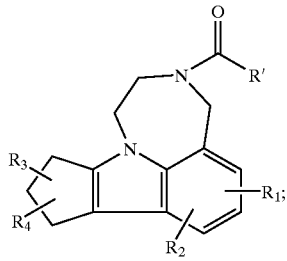

and further comprising reducing the acylated compound to provide a reduced acylated compound of the formula:

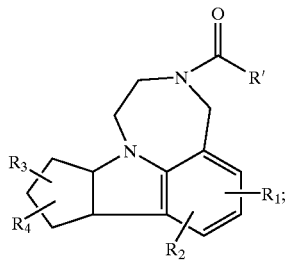

and deacylating the reduced acylated compound to provide a compound of the formula:

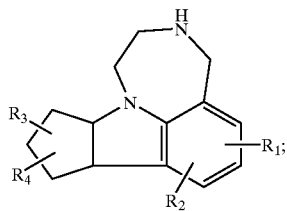

wherein $R_1$, $R_2$, $R_3$, and $R_4$ are as defined in claim 1.

6. The process of claim 5 further comprising the step of alkylating the compound of the formula:

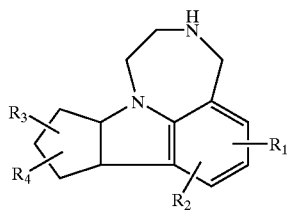

wherein $R_1$, $R_2$, $R_3$, and $R_4$ are as defined in claim 1, to provide an alkylated compound of the formula:

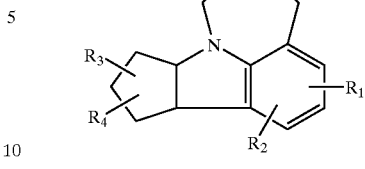

wherein R is an alkyl group of from 1 to 6 carbon atoms and $R_1$, $R_2$, $R_3$, and $R_4$ are as defined in claim 1.

7. The process of claim 1 comprising the steps a) through f) of claim 1 to produce a compound of the formula:

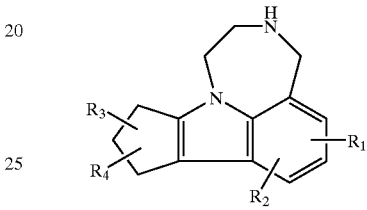

wherein $R_1$, $R_2$, $R_3$, and $R_4$ are as defined in claim 1, and further comprising the step of alkylating the compound to produce an alkylated compound of the formula:

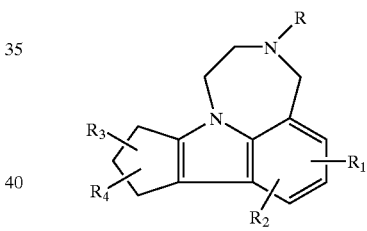

wherein R is an alkyl group of from 1 to 6 carbon atoms and $R_1$, $R_2$, $R_3$, and $R_4$ are as defined in claim 1.

8. The process of claim 1 wherein R is hydrogen and $R_1$, $R_2$, $R_3$, and $R_4$ are as defined in claim 1.

9. The process of claim 1 wherein R, $R_1$ and $R_3$ are hydrogen and $R_2$ and $R_4$ are as defined in claim 1.

10. The process of claim 1 wherein R, $R_1$, $R_2$, $R_3$, and $R_4$ are each hydrogen.

* * * * *